US010527637B2

(12) United States Patent
Fujita et al.

(10) Patent No.: US 10,527,637 B2
(45) Date of Patent: Jan. 7, 2020

(54) AUTOMATIC ANALYSIS DEVICE

(71) Applicant: Hitachi High-Technologies Corporation, Minato-ku, Tokyo (JP)

(72) Inventors: Hiroki Fujita, Tokyo (JP); Toshiharu Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/549,741

(22) PCT Filed: Feb. 5, 2016

(86) PCT No.: PCT/JP2016/053438
§ 371 (c)(1),
(2) Date: Aug. 9, 2017

(87) PCT Pub. No.: WO2016/140013
PCT Pub. Date: Sep. 9, 2016

(65) Prior Publication Data
US 2018/0017588 A1 Jan. 18, 2018

(30) Foreign Application Priority Data
Mar. 5, 2015 (JP) ................................. 2015-043088

(51) Int. Cl.
*G01N 35/04* (2006.01)
*G01N 35/10* (2006.01)
*G01N 35/00* (2006.01)

(52) U.S. Cl.
CPC ......... *G01N 35/0092* (2013.01); *G01N 35/04* (2013.01); *G01N 35/1002* (2013.01);
(Continued)

(58) Field of Classification Search
None
See application file for complete search history.

(56) References Cited

U.S. PATENT DOCUMENTS

2005/0207938 A1 9/2005 Hanawa et al.
2012/0301359 A1* 11/2012 Kraemer ................ G01N 35/04
422/64
(Continued)

FOREIGN PATENT DOCUMENTS

JP 2005-37171 A 2/2005
JP 2013-500489 A 1/2013
(Continued)

OTHER PUBLICATIONS

International Search Report (PCT/ISA/210) issued in PCT Application No. PCT/JP2016/053438 dated Apr. 26, 2016 with English-language translation (four (4) pages).
Japanese-language Written Opinion (PCT/ISA/237) issued in PCT Application No. PCT/JP2016/053438 dated Apr. 26, 2016 (three (3) pages).

*Primary Examiner* — Kathryn Wright
(74) *Attorney, Agent, or Firm* — Crowell & Moring LLP

(57) ABSTRACT

Provided is an automatic analysis device that enables a reagent to be reliably loaded in and loaded out within a stipulated amount of time, even during analysis and without stopping the analysis, and that enables a reagent to be exchanged without causing a long wait for the operator. Provided is the automatic analysis device that comprises the following: a reagent cooling box that cools and holds a plurality of reagent containers, and that accommodates therein a reagent holder for movably holding the reagent containers which are inside the reagent cooling box and a reagent loader for loading the reagent containers into and out of the reagent cooling box by moving in a vertical direction with respect to the reagent cooling box; a reagent cooling box cover that covers the upper surface of the reagent cooling box and that has an opening through which the reagent loader can pass; an instruction means that provides instructions for the movement of the reagent loader; and a
(Continued)

control device that includes, within the time of one cycle, a first time slot in which an operation for analysis is carried out and a second time slot in which an operation for the loading in or out of the reagent containers is carried out, and that executes control so that the reagent loader is not moved if the driving of the reagent loader was instructed by the instruction means in the second time slot.

5 Claims, 9 Drawing Sheets

(52) U.S. Cl.
CPC ... *G01N 35/1009* (2013.01); *G01N 35/00722* (2013.01); *G01N 2035/0094* (2013.01); *G01N 2035/00891* (2013.01); *G01N 2035/1025* (2013.01)

(56) References Cited

U.S. PATENT DOCUMENTS

| | | | |
|---|---|---|---|
| 2014/0295562 A1 | 10/2014 | Wakamiya et al. | |
| 2015/0369833 A1 | 12/2015 | Nakasawa et al. | |
| 2016/0146846 A1* | 5/2016 | Fujita | C01N 35/00663 422/67 |

FOREIGN PATENT DOCUMENTS

| | | | | |
|---|---|---|---|---|
| JP | 2014-145677 A | 8/2014 | | |
| JP | 2014-194390 A | 10/2014 | | |
| WO | WO 2011/012657 A1 | 2/2011 | | |
| WO | WO-2015005356 A1 * | 1/2015 | ....... | G01N 35/00732 |

\* cited by examiner

AUTOMATIC ANALYSIS DEVICE

TECHNICAL FIELD

The present invention relates to an automated analyzer for performing qualitative/qualitative analysis of a biological sample such as blood or urine.

BACKGROUND ART

An automated analyzer adds a reagent specifically reacting with a specific component contained in a biological sample such as blood or urine, causes the reagent to react with the specific component, and measures an absorbance and an amount of luminescence of a reaction liquid, thereby performing quantitative/qualitative analysis.

Generally, the automated analyzer includes a reagent container depository that can store a plurality of reagents corresponding to a plurality of analysis items so as to enable the analysis to be performed with respect to the plurality of analysis items. An analyzer management operator mounts reagents necessary for analysis of a day in the reagent container depository in advance. However, if shortage of reagents occurs during the analysis, the operator interrupts the analysis to replace the reagent.

Meanwhile, the number of analysis items for the automated analyzer has recently increased, and the number of automated analyzers that can mount many reagent containers by downsizing each reagent container so as to serve as analyzers compatible with analysis having many analysis items has increased. If the number of reagent containers mounted in the analyzer increases, it is highly likely that the shortage of reagents occurs, compared with a conventional analyzer. To address the problem, there is known an automated analyzer including a mechanism that can automatically add a reagent container to a reagent container depository (see, for example, Patent Document 1).

CITATION LIST

Patent Literature

Patent Document 1: JP Patent Publication 2005-37171 A

SUMMARY OF INVENTION

Technical Problem

In the automated analyzer described in Patent Document 1, the reagent can be automatically added during the analysis. However, it is necessary to temporarily stop the reagent container depository (reagent cooler) in order to displace the reagent from a reagent container temporary depository to the reagent cooler, which requires the analysis to be temporarily interrupted or requires a user to wait until the analysis is over. Furthermore, even if sample dispensing is interrupted, the reagent cooler is not stopped until completion of dispensing of all reagents to already dispensed samples (to complete the analysis of the already dispensed samples for avoiding waste of the samples). For the period of time, the user is forced to wait.

As a process capability of the automated analyzer is enhanced and space saving is achieved, the consumption of reagents per analysis time increases. In addition, the reagent cooler and a reagent container displacement mechanism incessantly operate during the analysis. Owing to this, temporarily stopping the reagent cooler and the reagent container displacement mechanism due to frequent reagent replacement causes reduction of an analysis throughput. Needs grows to automatically replace the reagent to reduce operator's waiting time as much as possible without interrupting the analysis.

An object of the present invention is to provide an automated analyzer that can load and unload a reagent within a specified time even during analysis without interrupting the analysis and replace the reagent without keeping an operator waiting for a long period of time.

Solution to Problem

To address the problem, the present invention is characterized in that an automated analyzer includes: a reagent holder holding a plurality of reagent containers so as to be movable; a reagent cooler for cooling the reagent containers held on the reagent holder; a reagent loader moving vertically with respect to the reagent cooler in order to load and unload the reagent container to and from the reagent cooler; instruction means for instructing displacement of the reagent loader; and a control section for exercising control so as not to vertically displace the reagent loader when the instruction means instructs driving the reagent loader in a second period, wherein one cycle time includes a first period for implementing operation for analysis and the second period for implementing operation for loading/unloading the reagent container.

Advantageous Effects of Invention

According to the present invention, it is possible to implement loading/unloading of a reagent container while suppressing user waiting time within certain time even during analysis, and to improve user work efficiency. Objects other than the abovementioned object, configurations, and advantages will be readily apparent from the description of embodiments given below.

DESCRIPTION OF EMBODIMENTS

Figure 1:
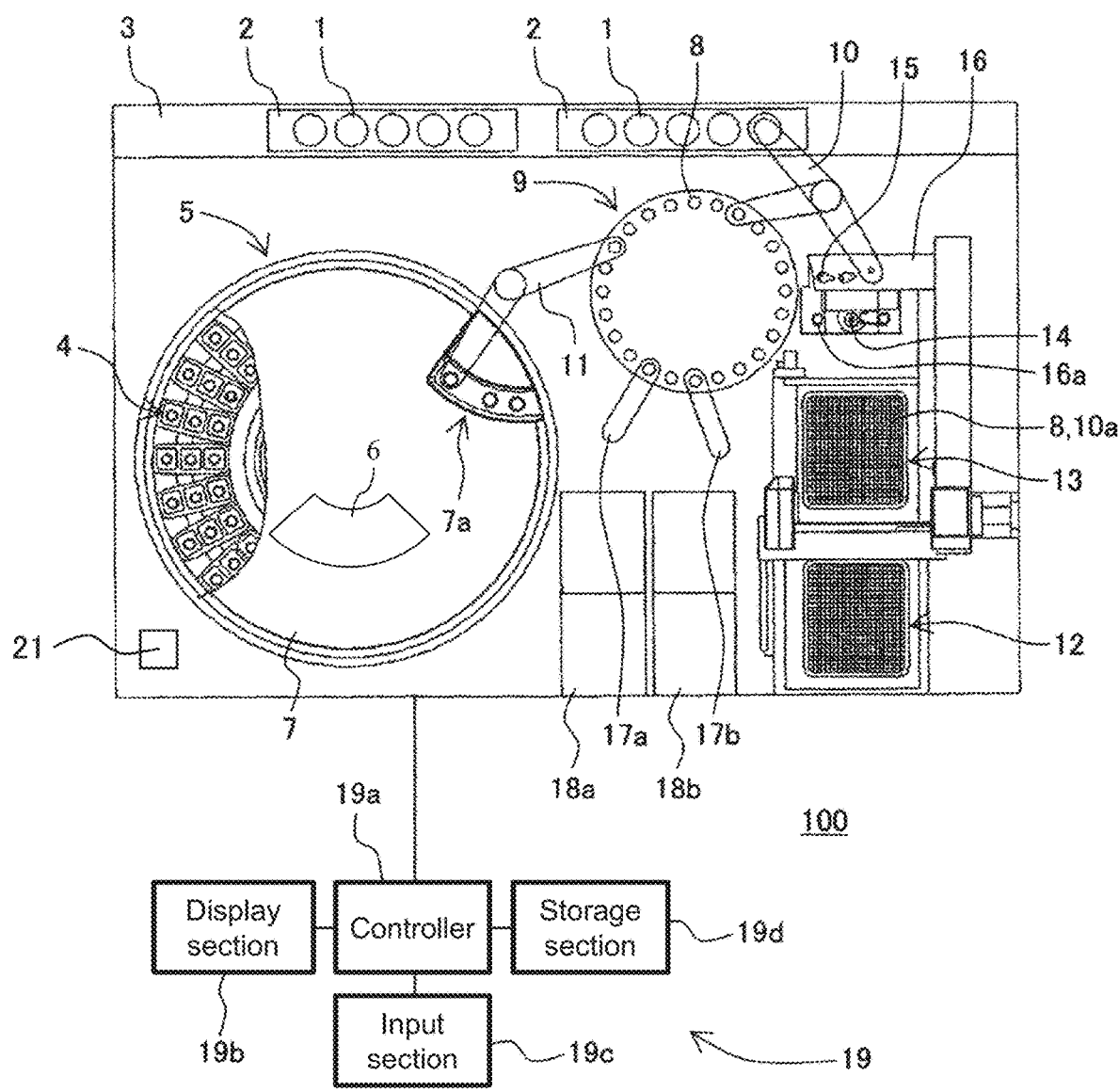
FIG. 1 is a configuration diagram of an automated analyzer according to an embodiment of the present invention.

A configuration and operation of an automated analyzer 100 according to an embodiment of the present invention will be described hereinafter. The automated analyzer 100 is intended to allow one system to implement different types of analysis, for example, biochemical analysis and immune analysis. It is noted that the same constituent elements are denoted by the same reference characters.

First, an overall configuration of the automated analyzer 100 according to the embodiment of the present invention will be described with reference to FIG. 1. FIG. 1 is a configuration diagram of the automated analyzer 100 according to the embodiment of the present invention. The automated analyzer 100 includes a rack transport line 3 transporting a sample container rack 2, a reagent cooler 5 a reagent loader 6, an incubator disk 9, a sample dispensing mechanism 10, a reagent dispensing mechanism 11, a reaction container/sample dispensing chip storage section 12, a replacement/supplementation reaction container/sample dispensing chip storage section 13, a reaction container stirring mechanism 14, a disposal hole 15, a transport mechanism 16, nozzles 17a, 17b, detection units 18a, 18b, and a control section 19. It is noted that an automated analyzer may have another configuration if the configuration can realize the present invention and enables a plurality of reagent containers to be held.

The sample container rack 2 stores a plurality of sample containers 1 each storing a biological sample (hereinafter, referred to as "sample") such as blood or urine. The rack transport line 3 transports the sample container rack 2.

The reagent cooler 5 (reagent container holding section) is covered with a reagent cooler cover 7, and stores a plurality of reagent containers 4 storing various reagents used for reagent analysis in a condition of keeping the reagent containers 4 at a constant temperature. In the present embodiment, the reagent cooler 5 is configured with an outer circumferential holder 51 that has positions 53 therein for holding the reagent containers 4 on a circumference of a circle and can be driven to rotate and an inner circumferential holder 52 that has positions for fixedly holding the reagent containers 4. Furthermore, the reagent loader 6 is provided adjacent to the inner circumferential holder 52 as described later, and a motor vertically driving the reagent loader 6 is provided. Moreover, a reagent container opening mechanism (not shown) for opening the reagent containers 4 is provided in the reagent cooler 5, whereby it is possible to open/close a lid of each reagent container 4 in the reagent cooler 5 and to suppress degradation of the reagents. It is noted that the reagent cooler 5 is not limited to a disk type but may be a serial type of arranging the reagent containers 4 in one or more lines.

The reagent loader 6 is provided in an inner circumferential portion of the reagent cooler 5. In addition, a reagent container displacement mechanism 20 for displacing the reagent container 4 between the reagent cooler 5 and the reagent loader 6 is provided near the reagent cooler 5 and the reagent loader 6 in a movable manner. When one reagent container 4 is loaded, the reagent container displacement mechanism 20 transports the loading target reagent container 4 from the reagent loader 6 to the outer circumferential holder 51. When one reagent container 4 is unloaded, the reagent container displacement mechanism 20 transports the reagent container 4 from the outer circumferential holder 51 to the reagent loader 6. Detailed configurations of the reagent loader 6 and the reagent container displacement mechanism 20 will be described later with reference to FIG. 2.

The incubator disk 9 has a plurality of container holding holes that can store a plurality of reaction containers 8 for mixing the sample with reagents on a circumference of a circle, and is driven to intermittently rotate so as to locate each reaction container 8 at a predetermined position as analysis progresses. In a portion in which the incubator disk 9 is stopped, process necessary for steps such as sample or reagent dispensing, stirring, and analysis steps is implemented.

The sample dispensing mechanism 10 includes an arm section driven to rotate and vertically driven, and a nozzle section sucking and discharging the sample. A sample dispensing chip 10a can be detachably attached to a tip end of the nozzle section. The sample dispensing mechanism 10 moves downward the nozzle section with respect to the sample container 1 transported to a sample dispensing position by the rack transport line 3 to suck a predetermined amount of the sample, and rotates the arm section to discharge the sample to one reaction container 8 located at a predetermined position on the incubator disk 9.

The reagent dispensing mechanism 11 includes a nozzle section sucking and discharging the reagents. The reagent dispensing mechanism 11 discharges, through a reagent cooler cover opening 7a provided in the reagent cooler cover 7 to the reaction container 8 located at the predetermined position on the incubator disk 9, predetermined amounts of the reagents sucked from the reagent container 4 by operation for horizontal driving, perpendicular driving, and suction/discharging.

The reaction container stirring mechanism 14 stirs a reaction liquid stored in the reaction container 8 taken out from the incubator disk 9.

The reaction container/sample dispensing chip storage section 13 stores a plurality of unused reaction containers 8 and a plurality of unused sample dispensing chips 10a. The reaction container/sample dispensing chip storage section 12 is prepared for replacing or refilling the reaction container/sample dispensing chip storage section 13. When the sample dispensing chip 10a is attached to the nozzle tip end of the sample dispensing mechanism 10 and the sample in the sample container is sucked, the used sample dispensing chip 10a is disposed of from the disposal hole 15. The used reaction container 8 completed with analysis is similarly disposed of from the exhaust hole.

The transport mechanism 16 includes a gripper section gripping the sample dispensing chip 10a and the reaction container 8 stored in the reaction container/sample dispensing chip storage section 13. The transport mechanism 16 also includes a drive section transporting the gripper mechanism along XYZ axes. Specifically, the transport mechanism 16 is provided to be movable in X-axis, Y-axis, and Z-axis directions (not shown). The transport mechanism 16 transports the reaction container 8 stored in the reaction container/sample dispensing chip storage section 13 to the incubator disk 9, disposes of the used reaction container 8 to the disposal hole 15, and transports the unused sample dispensing chip 10a to a chip attachment position 16a.

The nozzles 17a and 17b suck the reaction liquids mixed in the reaction containers 8 of the incubator disk 9. The nozzles 17a and 17b feed the reaction liquids to the respective detection units 18a and 18b by being driven to rotate or vertically driven. The detection units 18a and 18b perform detection process on the reaction liquids sucked and fed by the nozzles 17a and 17b to detect a specific component.

An operator operates a reagent loader switch 21 to notify the automated analyzer 100 of start of loading and unloading of the reagent container 4. Detailed process implemented when the reagent loader switch 21 is depressed will be described later with reference to FIG. 8.

The control section 19 exercises control over the entire operation of the automated analyzer 100. The control section 19 includes a controller 19a, a display section 19b, an input section 19c, and a storage section 19d. A detailed configuration of the control section 19 will be described later with reference to FIG. 4.

Figure 2:
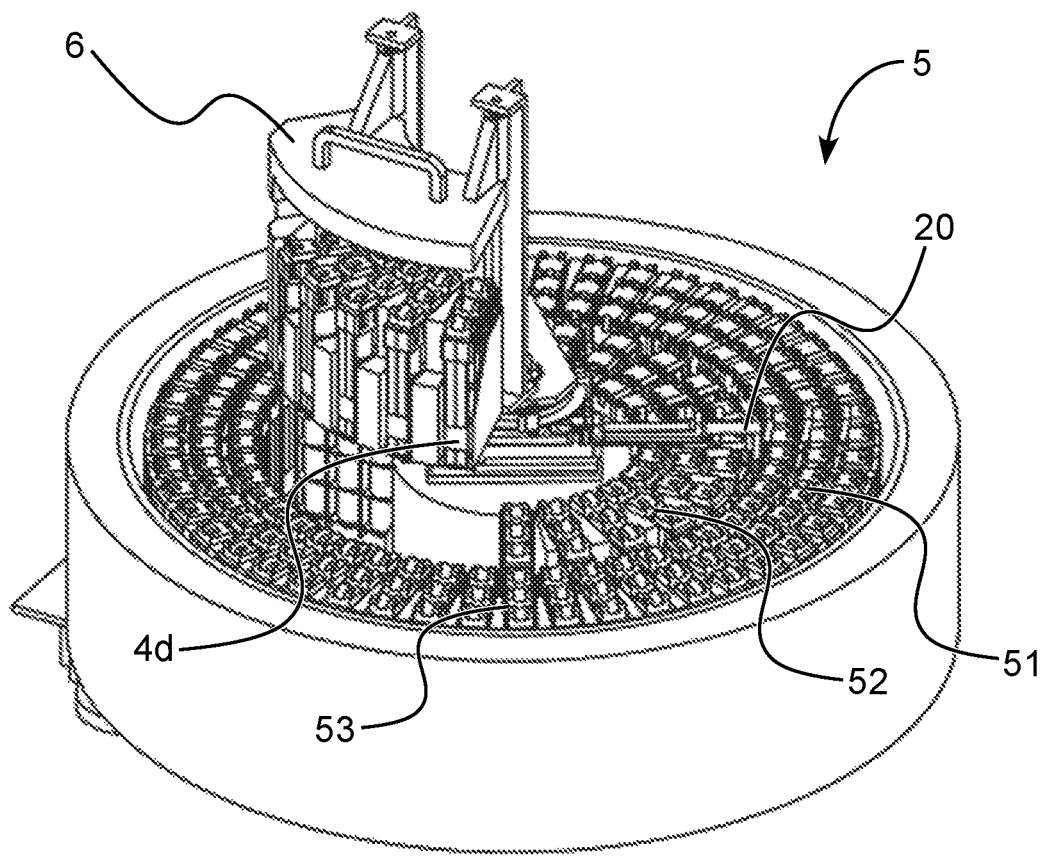
FIG. 2 is an explanatory diagram of a configuration of a peripheral part of a reagent cooler used in the automated analyzer according to the embodiment of the present invention.

A configuration of a peripheral part of the reagent cooler 5 (reagent container holding section) used in the automated analyzer 100 according to the embodiment of the present invention will next be described with referring to FIG. 2. FIG. 2 is an explanatory diagram of a configuration of the reagent cooler 5 used in the automated analyzer 100 according to the embodiment of the present invention.

The reagent cooler 5 includes the outer circumferential holder 51 that holds a plurality of reagent containers 4 on the circumference of a circle and that can be driven to rotate, the inner circumferential holder 52 that fixedly holds the reagent containers 4. The reagent cooler 5 also includes the reagent loader 6 that is provided on an inner circumferential side of the outer circumferential holder 51 (near a center of the reagent cooler 5) and that can be driven vertically. Preferably, the inner circumferential holder 52 and the reagent loader 6 are provided on the same circumference of a circle.

The reagent loader 6 has a plurality of positions into which the reagent containers 4 are inserted, and can vertically move the reagent container 4 inserted into each position and can transfer the reagent container 4 inside or outside of the reagent cooler 5. While the reagent loader 6 shown in FIG. 2 is configured such that five positions are provided and up to five reagent containers 4 can be installed, the number of the installable reagent containers 4 is not limited to five.

Furthermore, a reader (not shown) is provided near the reagent loader 6 to read out an individual identification label 4d (RFID tag in the present embodiment) adhering to a wall surface of each reagent container 4 and to transmit identification information thereon to the controller 19a of the control section 19. It is noted that a barcode label or the like may be used as the individual identification label 4d for the reagent container 4. The identification information recorded in the individual identification label 4d includes a reagent identification number (identification code) for identifying reagents stored in the reagent container 4, inspection item names corresponding to the stored reagents, reagent identification codes, a lot number, a sequence number, and the like.

The reagent container displacement mechanism 20 radially displaces each reagent container 4 among the outer circumferential holder 51, the inner circumferential holder, and the reagent loader 6. The reagent container displacement mechanism 20 can rotationally move about the center of the reagent cooler 5 that serves as an axis, and access all positions and all positions in the outer circumferential holder 51, the inner circumferential holder 52, and the reagent loader within the reagent cooler 5. While the reagent cooler 5 includes one reagent container displacement mechanism 20 in the present embodiment, the reagent cooler 5 may include a plurality of reagent container displacement mechanisms 20. Further, while the reagent container displacement mechanism 20 is configured to be independent of the reagent cooler 5 and the reagent loader 6 in the present embodiment, the reagent container displacement mechanism 20 may be a mechanism configured to be included in the reagent cooler 5 or in the reagent loader 6.

Analysis operation implemented by each of the outer circumferential holder 51, the reagent loader, and the reagent container displacement mechanism 20 of the reagent cooler 5 will next be described in accordance with analysis steps.

First, to dispense a first reagent, the outer circumferential holder 51 rotates to displace the target reagent container 4 to a position at which the reagent dispensing mechanism 11 can access the reagent container 4 (displacement 1 for reagent dispensing). The reagent dispensing mechanism 11 accesses the reagent container 4 installed in the reagent cooler 5, sucks the reagent, and then dispenses the first reagent to the reaction container 8 installed in the incubator disk 9.

When sample dispensing is over and reaction time specified for every analysis item passes, a second reagent is dispensed to the reaction container 8 on the incubator disk 9. In a case of implementing immune analysis, the second reagent contains magnetic particles; therefore, it is necessary to implement stirring process for dispersing the magnetic particles in the liquid before dispensing. In the automated analyzer 100 according to the present embodiment, a stirring mechanism for stirring the magnetic particles is provided near the inner circumferential holder 52 of the reagent cooler 5. Owing to this, before and after stirring of the magnetic particles, the reagent container displacement mechanism 20 displaces the reagent container 4 between the inner circumferential holder 52 and the outer circumferential holder 51. At timing of stirring the magnetic particles, the outer circumferential holder 51 rotates and the reagent container displacement mechanism 20 implements operation for reagent container displacement to displace the target reagent container toward the inner circumferential holder 52, thereby displacing the reagent container 4 to a magnetic particle stirring position at which the magnetic particle stirring mechanism can access the reagent container 4.

The magnetic particle stirring mechanism accesses the reagent container 4 displaced to the magnetic particle stirring position to stir the magnetic particles. To displace the reagent container 4 completed with stirring of the magnetic particles from the inner circumferential holder 52 to the outer circumferential holder 51, the reagent cooler 5 is driven to rotate to displace a vacant position to an access position of the reagent container displacement mechanism 20 (displacement after stirring of magnetic particles). To dispense the second reagent after the reagent container is displaced to the outer circumferential holder 51, the reagent cooler 5 rotates to displace the target reagent container 4 to a position at which the reagent dispensing mechanism 11 can access the target reagent container 4 (displacement 2 for reagent dispensing). The reagent dispensing mechanism 11 accesses the reaction container 4 installed in the reagent cooler 5, sucks the reagent, and then dispenses the second reagent to the reaction container 8 installed on the incubator disk 9. In this way, the reagent cooler 5 and the reagent container displacement mechanism 20 operate, thereby performing a series of reagent dispensing operation in the analysis.

In the automated analyzer 100 according to the present embodiment, only one reagent container displacement mechanism 20 is provided from the viewpoint of space saving, and the one reagent container displacement mechanism 20 implements both the displacement of the reagent container for access to the magnetic particle stirring mechanism and the displacement of the reagent container to/from the reagent loader 6 for reagent loading/unloading. Owing to this, at timing at which the reagent container displacement mechanism 20 is implementing the displacement of the reagent container for the analysis, the reagent container cannot be displaced to the reagent loader 6 for loading/unloading. It applies to the outer circumferential holder 51. To implement the loading/unloading of the reagent container without delay in analysis operation during implementation of the analysis, timing at which the analysis operation is not implemented is allocated to the reagent container loading/unloading by the outer circumferential holder 51 and the reagent container displacement mechanism.

At the reagent container loading/unloading timing, the outer circumferential holder 51 is driven to rotate to locate one position to be close to the reagent loader 6. Subsequently, the reagent container displacement mechanism is caused to operate. In a case of reagent loading, the reagent container displacement mechanism displaces the reagent container from the position of the reagent loader 6 to a vacant position of the outer circumferential holder 51. In a case of reagent unloading, the reagent container displacement mechanism displaces the reagent container from the position on the outer circumferential holder 51 to a vacant position on the reagent loader 6.

Figure 3:
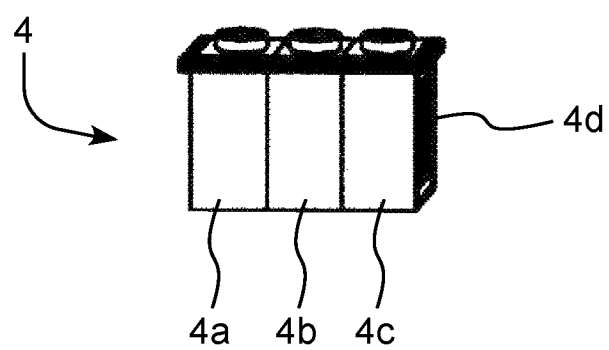
FIG. 3 is a configuration diagram of a reagent container used in the automated analyzer according to the embodiment of the present invention.

A configuration of the reagent container 4 used in the automated analyzer 100 according to the embodiment of the present invention will next be described with reference to FIG. 3. FIG. 3 is a configuration diagram of the reagent container 4 used in the automated analyzer 100 according to the embodiment of the present invention.

Each reagent container 4 is configured with small bottles 4a to 4c storing a plurality of types of (three types in the present embodiment) reagents. One reagent container 4 (that is, the small bottles 4a to 4c) stores a set of reagents necessary for one analysis item. Examples of the reagents stored in the bottles 4a to 4c of the reagent container 4 include a luminous label reagent containing a luminous label and a magnetic particle reagent containing magnetic particles.

Figure 4:
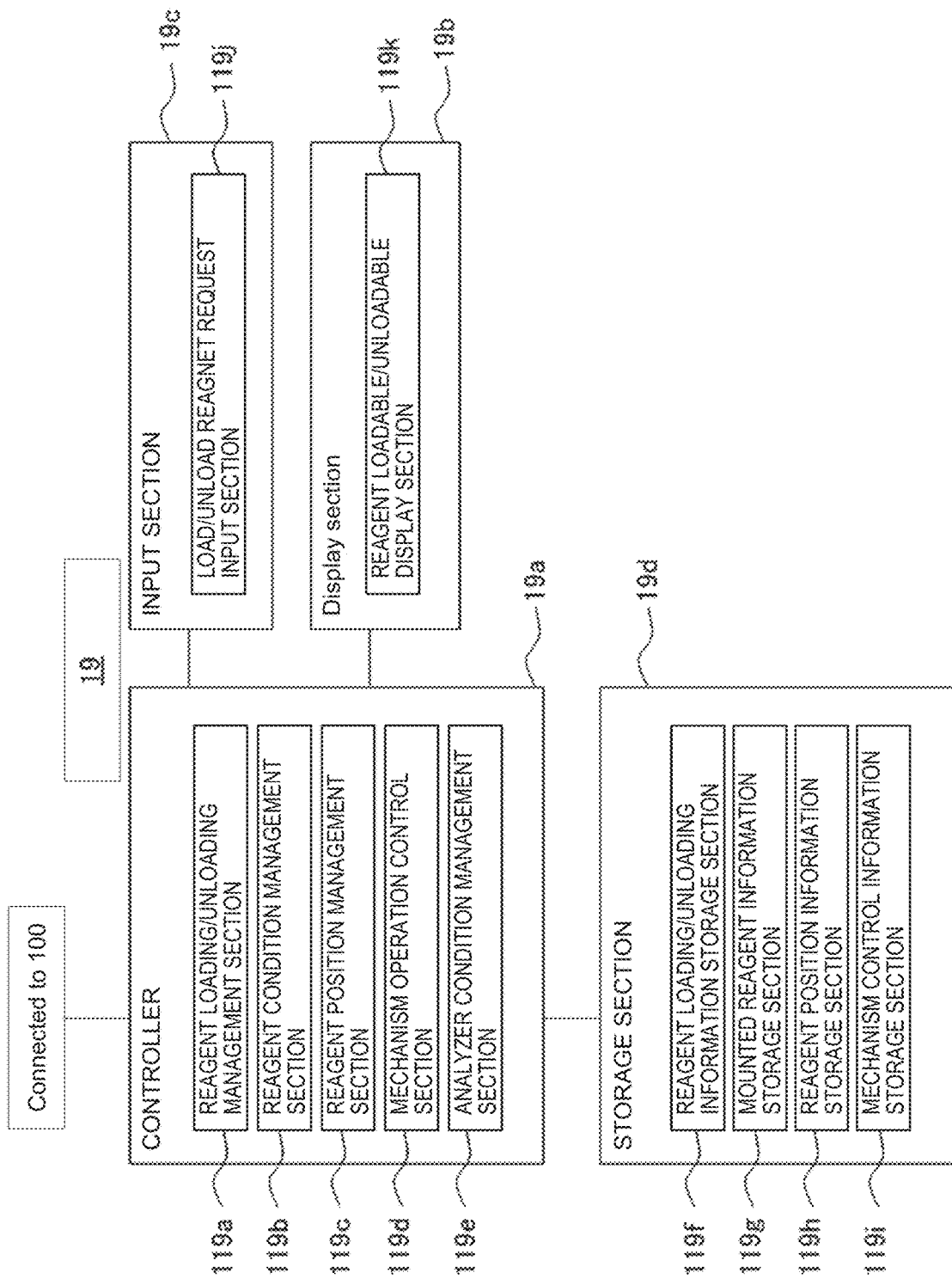
FIG. 4 is an explanatory diagram of functions of a control section used in the automated analyzer according to the embodiment of the present invention.

Functions of the control section 19 used in the automated analyzer 100 according to the embodiment of the present invention will next be described with reference to FIG. 4. FIG. 4 is a functional block diagram of the control section 19 used in the automated analyzer 100 according to the embodiment of the present invention. The control section 19 exercises control over the entire operation of the automated analyzer 100.

The control section 19 exercises control over the loading/unloading of the reagent container 4 and sample analysis process on the basis of a preset program or an operator's command input by the input section 19c or the like. The control section 19 includes the controller 19a that exercises control over operation of the automated analyzer 100 and process for an analysis result, the input section 19c to which information/setting about the sample and analysis items is input and which transmits the information to the controller 19a as needed, the display section 19b that displays an analysis-related setting input screen and the analysis result, and the storage section 19d that stores the analysis-related setting, the information on the sample, the reagents, and the like, the analysis result, and the like.

The storage section 19d includes a reagent loading/unloading information storage section 119f, a mounted reagent information storage section 119g, a reagent position information storage section 119h, and a mechanism control information storage section 119i.

The mounted reagent information storage section 119g is a functional block that stores reagent use history information and identification information on the reagent container 4 to be associated with each other. Here, the reagent use history information is reagent information on the reagents stored in a plurality of reagent containers 4 mounted in the reagent cooler 5 or installed in the reagent loader 6 and includes at least information about a reagent condition indicating whether each reagent can be used. In other words, the mounted reagent information storage section 119g stores the identification information on the reagent container and the information about the reagent condition to be associated with each other.

A reading mechanism such as an RFID reader or a barcode reader is provided in a moving route of the reagent loader. The reading mechanism can read out the individual identification information on the reagent container 4 displaced by the reagent loader. When the reading mechanism reads out the identification information and the information about the reagent condition from the individual identification information 4d for the reagent container loaded into the reagent cooler 5, the individual identification information is transmitted to the storage section 19d via the controller 19a and stored in the mounted reagent information storage section 119g. Conversely, when the reading mechanism reads out the individual identification information for the reagent container unloaded from the reagent cooler 5, the individual identification information and the associated reagent use history information are deleted from the mounted reagent information storage section 119g. It is noted that the information about the reagent condition may be read out from the individual identification information 4d, or may be retrieved and obtained from information stored in the storage section on the basis of the identification information read out from the individual identification information 4d.

The reagent loading/unloading information storage section 119f is a functional block that stores information about a displace reagent request on the reagent container 4 and the identification information on the reagent container 4 to be associated with each other. Here, the information about the displace reagent request is information on a plurality of reagent containers 4 installed in the reagent cooler 5 or the reagent loader 6. The reagent displacement request information includes at least information about a load reagent request and information about an unload reagent request. The reagent loading/unloading information storage section 119f stores the information about the load reagent request and the information about the unload reagent request of which the reagent loading/unloading information storage section 119f is notified by a reagent loading/unloading management section 119a to be described later. Furthermore, the input section 19c is notified of a reagent unloading instruction from the operator via means such as a dedicated screen or a switch, and the reagent unloading instruction is stored in the reagent loading/unloading information storage section 119f as the information about the unload reagent request.

When the reagent container displacement mechanism 20 operates to displace the to-be-loaded reagent container 4 from the reagent loader 6 to the outer circumferential holder 51, the information about the load reagent request on the reagent container 4 is deleted from the reagent loading/unloading information storage section 119f. Further, when the reagent container 4 to be unloaded from the reagent cooler 5 is displaced from the outer circumferential holder 51 to the reagent loader 6, the information about the unload reagent request on the reagent container 4 is deleted from the reagent loading/unloading information storage section 119f.

The reagent position information storage section 119h is a functional block that stores information about a reagent position condition. The information about the reagent position condition is information as to whether the reagent container is held in a position on the outer circumferential holder 51, the inner circumferential holder 52, or the reagent loader.

The mechanism control information storage section 119i is a functional block that stores information about mechanism control to be described later.

The controller 19a includes the reagent loading/unloading management section 119a, a reagent condition management section 119b, a reagent position management section 119c, a mechanism operation control section 119d, and an analyzer condition management section 119e.

The reagent loading/unloading management section 119a is a functional block that manages the loading/unloading of each reagent container 4 in the reagent cooler 5 (including the reagent loader 6) on the basis of a reagent condition of the reagent container 4 and a vacant condition of each position. Specifically, the reagent loading/unloading management section 119a plans the reagent displacement request information (reagent load request information and reagent unload request information) according to the reagent condition information acquired from the mounted reagent information storage section 119g and to the reagent position condition information acquired from the reagent position information storage section 119h. The reagent loading/unloading management section 119a stores the created information about the displace reagent request in the reagent loading/unloading information storage section 119f as the information about the load reagent request or the information about the unload reagent request. The reagent loading/unloading management section 119a manages a progress of each step when the reagent container displacement mechanism 20 or the reagent loader 6 implements the reagent container loading/unloading. Planning of the reagent loading/unloading will be described later in detail.

Here, the information about the load reagent request includes at least information regarding which one of loading target reagent containers held at each position is loaded to which one of positions on the reagent loader 6. The information about the unload reagent request includes at least information regarding which one of reagent containers held at each position is unloaded to which positions of the outer circumferential holder 51.

The reagent condition management section 119b is a functional block that provides the information about a reagent condition indicating a latest condition of the reagent container 4 in the reagent cooler 5 (including the reagent loader 6). When the reagent loading/unloading management section 119a instructs the reagent condition management section 119b to obtain the information about the reagent condition, the reagent condition management section 119b obtains the mounted reagent information from the mounted reagent information storage section 119g. The reagent condition management section 119b updates the information about the reagent condition on the basis of the obtained mounted reagent information. The reagent condition management section 119b notifies the reagent loading/unloading management section 119a of the updated information about the reagent condition.

The reagent position condition management section 119c is a functional block that provides the information about the reagent position condition indicating a condition of each position in the reagent cooler 5 (including the reagent loader 6). When the reagent loading/unloading management section 119a instructs the reagent position management section 119c to obtain the information about the reagent position condition, the reagent position management section 119c obtains, from the reagent position information storage section 119h, the information (information about the reagent position) as to whether the reagent container is installed at any position of the outer circumferential holder 51 and the inner circumferential holder 52 or any position of the reagent loader 6. The reagent position management section 119c updates the information about the reagent position condition on the basis of the obtained information the reagent position, and notifies the reagent loading/unloading management section 119a of the updated information about the reagent position condition.

The mechanism operation control section 119d is a functional block that controls the outer circumferential holder 51, the reagent loader 6, and the reagent container displacement mechanism 20 to operate. Specifically, the mechanism operation control section 119d plans to drive the outer circumferential holder 51 to rotate, vertically drive the reagent loader 6, and cause the reagent container displacement mechanism 20 to operate on the basis of the information about the displace reagent request obtained from the reagent loading/unloading information storage section 119f and information about the analyzer condition obtained from the analyzer condition management section 119e to be described later. Created mechanism control information is stored in the mechanism control information storage section 119i. The mechanism operation control section 119d extracts the mechanism control information from the mechanism control information storage section 119i at timing of implementing controlling the outer circumferential holder 51, the reagent loader 6, and the reagent container displacement mechanism 20 to operate, and instructs the mechanisms to be controlled on the basis of the mechanism control information.

The analyzer condition management section 119e is a functional block that provides the information about the analyzer condition. The analyzer condition management section 119e manages information as to whether analysis is being implemented as the information about the analyzer condition to be provided.

The input section 19c includes a load/unload reagent request input section 119j that enables the operator to instruct the automated analyzer 100 to load/unload the reagent container. While the input section is not particularly limited to a specific example, it is possible to instruct the automated analyzer 100 to unload the reagent designated by the operator via, for example, depression of the loader switch arranged near the reagent loader 6 or the dedicated screen.

The display section 19b can display a reagent loadable/unloadable display section 119k on the screen. The display section will be described later in detail.

Figure 5:
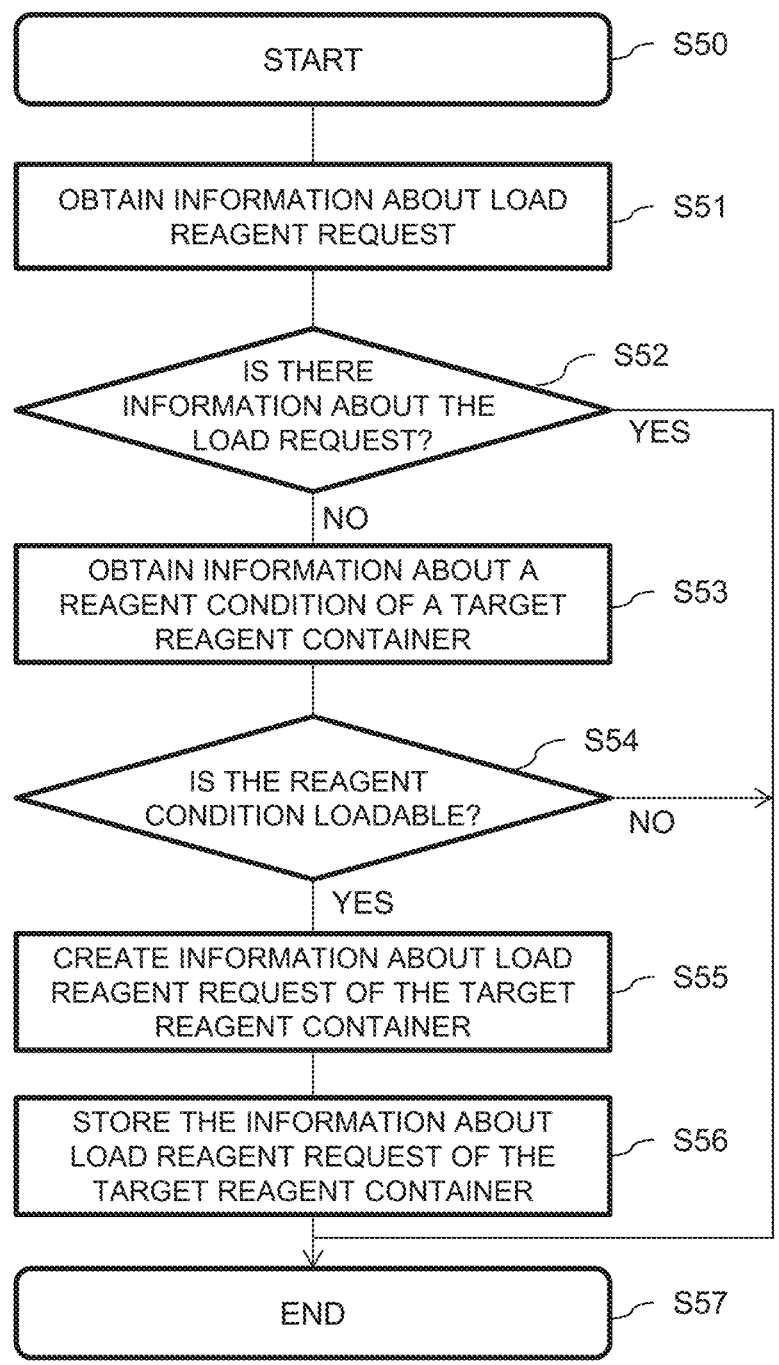
FIG. 5 is a flowchart diagram illustrating logic for creating a load reagent request at a time of planning to load a reagent container in the automated analyzer according to the embodiment of the present invention.
Figure 6:
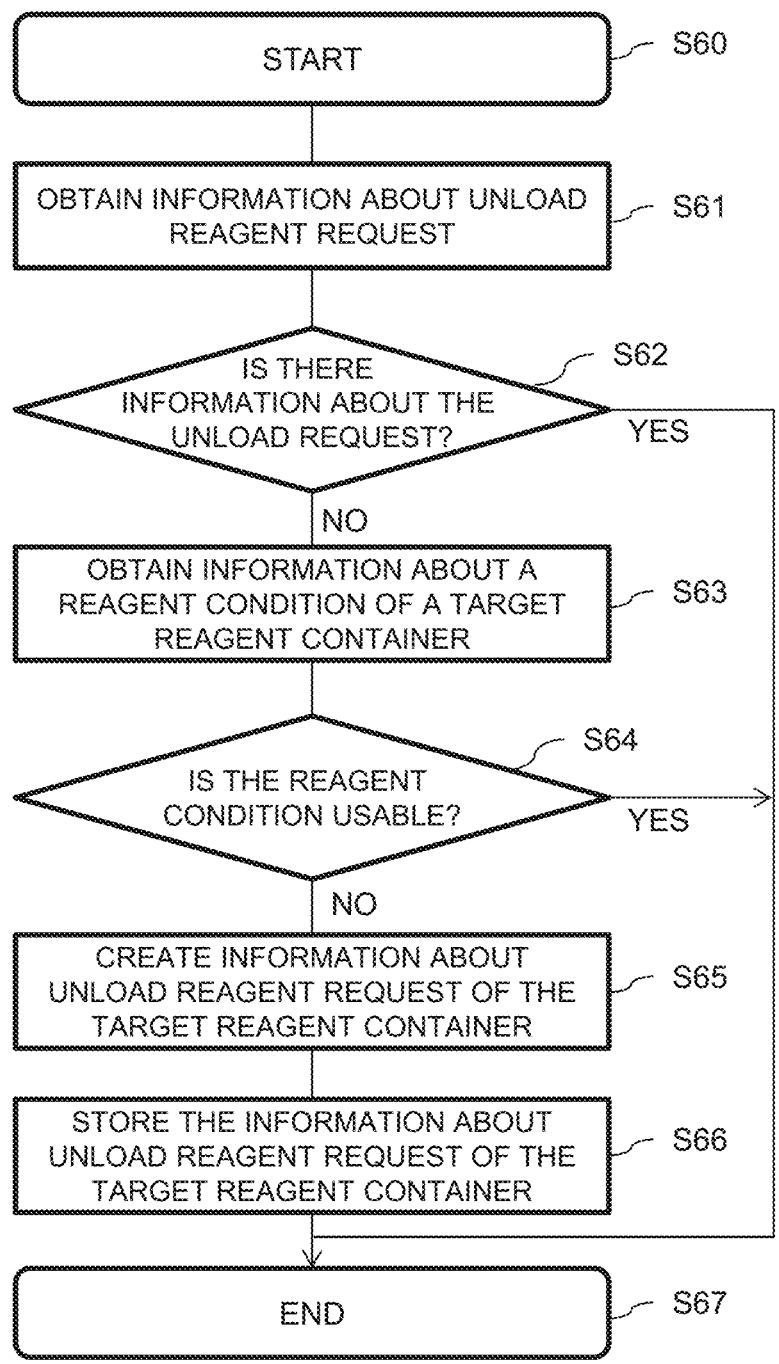
FIG. 6 is a flowchart diagram illustrating logic for creating an unload reagent request at a time of planning to unload the reagent container in the automated analyzer according to the embodiment of the present invention.
Figure 7:
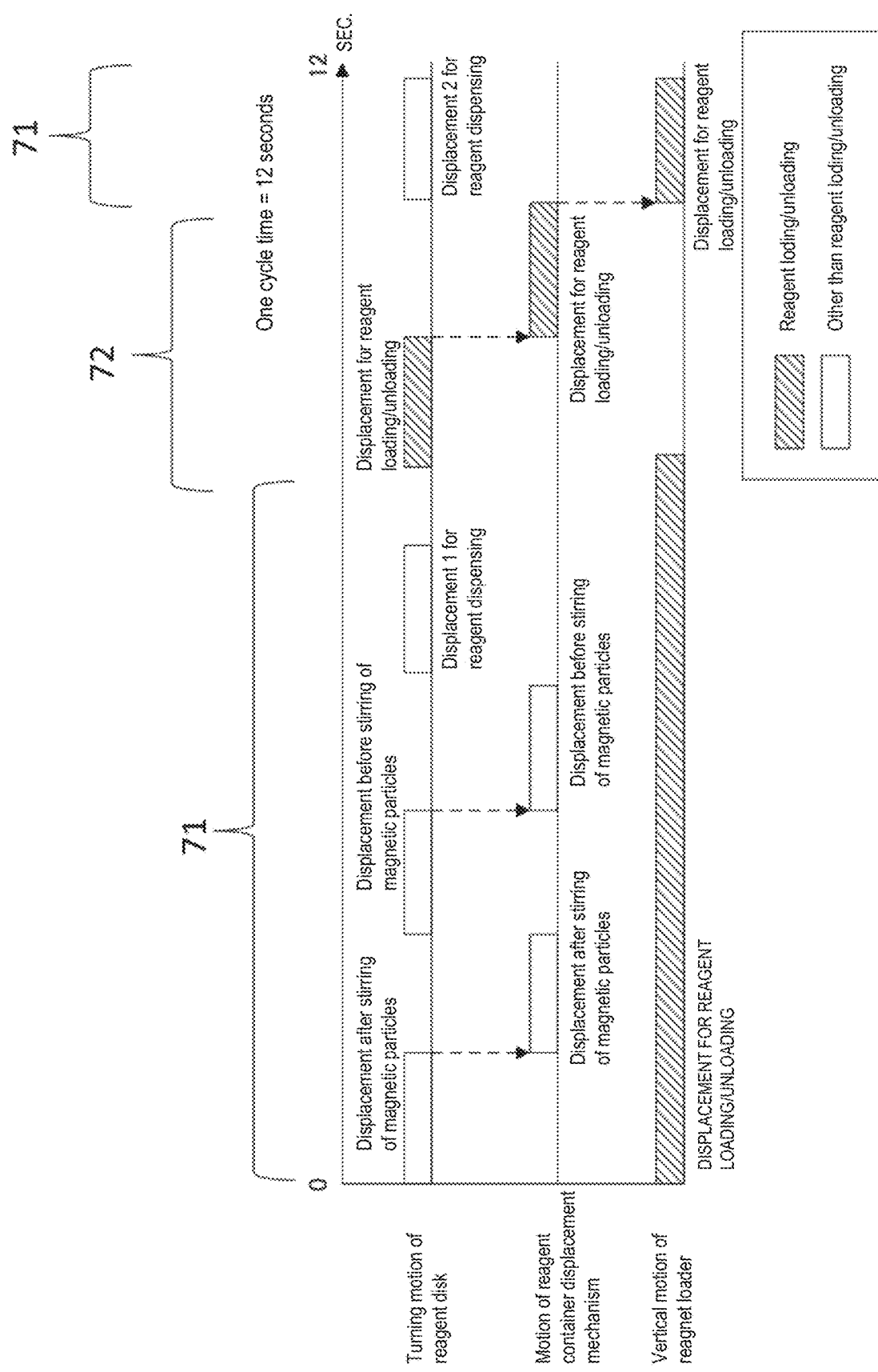
FIG. 7 is a time chart diagram illustrating timing of mechanism operation implemented by a reagent cooler, a reagent loader, and a reagent container displacement mechanism in the automated analyzer according to the embodiment of the present invention.

Planning and implementation of the loading and unloading of the reagent container 4 in the automated analyzer 100 according to the embodiment of the present invention will next be described with reference to FIGS. 5 to 7.

A method of creating, by the reagent loading/unloading management section 119a, the information about the load reagent request for loading the reagent container on the reagent loader 6 to the outer circumferential holder 51 will be described with reference to FIG. 5.

First, when the reader detects presence of the to-be-loaded reagent container by moving downward the reagent loader 6 in a condition in which the reagent container 4 is installed on the reagent loader 6, process is started (Step S50). The reagent loading/unloading management section 119a obtains the already created information about the load reagent request from the reagent loading/unloading information storage section 119f (Step S51), and confirms whether there is information about a load reagent request on the reagent container (Step S52). When the information about the load reagent request is already stored for the loading target reagent container 4 (Step S52; YES), the process is ended.

When the information about the load reagent request is not stored in Step S20 (Step S52; NO), the reagent loading/ unloading management section 119a obtains the information about the reagent condition on the target reagent container 4 from the mounted reagent information storage section 119g (Step S53). The information about the reagent condition at a time of loading can be classified into information about three conditions, i.e., (1) a loadable condition in which the target reagent container 4 can be loaded to the device, (2) an unloadable condition in which the target reagent container cannot be loaded to the device, and (3) a temporary unloadable condition in which the target reagent container cannot be temporarily loaded to the device. It is confirmed whether the reagent condition of the target reagent container 4 is the loadable condition out of these reagent conditions. When the obtained information about the reagent condition on the reagent container 4 does not indicate the loadable condition (Step S54; NO), it is not appropriate to load the reagent container 4 to the outer circumferential holder 51. Therefore, the process is ended and the reagent container 4 is left mounted on the reagent loader 6.

It is noted that (2) the unloadable condition means the reagent condition in which the reagent container 4 is continuously unusable in the future as well since the reagent has expired or none of the reagents is left. (3) The temporarily unloadable condition means the reagent condition in which the reagent is unusable for a resolvable reason such as presence of bubbles on a liquid surface or temporary inability to read out the individual identification information. (1) The loadable condition means the reagent condition other than the above conditions.

When the reagent condition information on the reagent container 4 indicates the loadable condition in Step S40 (Step S54; YES), the reagent loading/unloading management section 119a obtains the information about the reagent position condition from the reagent position information storage section 119h. The reagent loading/unloading management section 119a determines which position of the outer circumferential holder 51 the target reagent container 4 is loaded to on the basis of the information about the reagent condition and the information about the reagent position condition, and creates the information about the load reagent request (Step S55). The reagent loading/unloading management section 119a then instructs the created information about the load reagent request to be stored in the reagent loading/unloading information storage section 119f (Step S56), thereby ending the process (Step S57).

A series of steps described above is implemented to all the reagent containers 4 installed at the positions of the reagent loader 6 per cycle. Thus, when the reagent container to be loaded is installed on the reagent loader 6, it is possible to create a plan to load a new reagent container from a position of the reagent loader 6 to the vacant position of the reagent cooler 5 irrespective of whether the analysis is being implemented.

Regarding a method of determining a reagent loading order and installation positions of the reagent containers 4 when the loading target reagent containers 4 are loaded to the positions in the reagent cooler 5, the reagent containers 4 are loaded from the reagent loader 6 to vacant positions of the outer circumferential holder 51 in an ascending order of position numbers on the reagent loader 6 such that the reagent container held at the position having a lowest position number is loaded first when the reagent containers 4 are loaded from the reagent loader 6 to the reagent cooler 5. While it is described that the order of loading the reagent containers 4 to the reagent cooler 5 is the ascending order in the embodiment of the present invention, the loading order may be set by another logic such as a descending order of the position numbers. Further, as for the method of determining the positions on the outer circumferential holder 51 that is a loading destination, the first reagent container 4 is loaded to the position at the vacant position having a lowest position number out of the vacant positions of the outer circumferential holder 51, that is, the vacant positions of the reagent cooler 5 are used in an ascending order of the position numbers. While it is described that as for the method of determining the positions on the reagent cooler 5 as the loading destination, the order is the ascending order of the position numbers on the reagent cooler 5 in the embodiment of the present invention, the order is not limited to the ascending order but may be a descending order of the position numbers on the reagent cooler 5 or the like.

A method of creating, by the reagent loading/unloading management section 119a, the information about the unload reagent request for unloading the reagent container on the outer circumferential holder 51 to the reagent loader 6 will next be described with reference to FIG. 6.

When the operator instructs the automated analyzer 100 to unload the reagent container or when the controller 19 detects occurrence of the reagent container to be unloaded due to a change in the information about the reagent condition, process is started (Step S60). The reagent loading/ unloading management section 119a obtains the information about the unload reagent request from the reagent loading/ unloading information storage section 119f (Step S61), and confirms whether there is information about an unload reagent request included therein (Step S62). When the information about the unload reagent request for the unloading target reagent container 4 is already stored (Step S62; YES), the process is ended.

When the information about the unload reagent request is not stored in Step S120 (Step S62; NO), the reagent loading/ unloading management section 119a obtains the information about the reagent condition on the reagent container 4 from the mounted reagent information storage section 119g (Step S63). The information about the reagent condition at a time of unloading can be classified into information about three conditions, i.e., (1) a usable condition in which the reagent container 4 is usable for analysis, (2) an unusable condition in which the reagent container 4 is unusable for the analysis, and (3) a temporarily unusable condition in which the reagent container 4 is temporarily unusable for the analysis. It is confirmed whether the reagent condition of the target reagent container 4 is the usable condition out of these reagent conditions. When the obtained information about the reagent condition on the reagent container 4 indicates the usable condition (step S64; YES), the process is ended. It is noted that the conditions (1) to (3) are almost the same as contents of the information about the reagent condition identified by the loading condition shown in FIG. 5.

When the information about the reagent condition on the reagent container 4 does not indicate the usable condition in Step S140 (Step S64; NO), then the reagent loading/unloading management section 119*a* obtains the information about the reagent position condition from the reagent position information storage section 119*h*, and creates information about an unload reagent request on the reagent container 4 on the basis of the information about the reagent condition and the information about the reagent position condition (Step S65). The reagent loading/unloading management section 119*a* instructs the created information about the unload reagent request to be stored in the reagent loading/unloading information storage section 119*f* (Step S66), thereby ending the step (Step S67).

A series of steps described above is implemented to all the reagent containers 4 installed in the reagent cooler 5 whenever reagent dispensing process is implemented to the reagent containers held in the reagent cooler 5. It is thereby possible to create an implementation plan for displacing the loading target reagent containers from the positions of the outer circumferential holder 51 to the vacant positions of the reagent loader 6 irrespective of whether the analysis is being implemented.

An order of displacing the reagent containers 4 from the outer circumferential holder 51 of the reagent cooler 5 to the reagent loader 6 is determined by a factor for unloading the reagent containers 4 and position information on the outer circumferential holder 51. As the factor for unloading the reagent container 4, three types of factors are present, that is, an unloading factor by operator's designation, an unloading factor because the reagent container 4 becomes temporarily unusable, and an unloading factor because the reagent container 4 becomes unusable. Among these factors, the reagent container unloaded by operator's designation is highest in an order of priority, followed by the reagent container unloaded because the reagent container becomes temporarily unusable and the reagent container because the reagent container becomes unusable. If the factor for unloading the reagent container 4 is the same among a plurality of reagent containers 4, the reagent container at the position having the lowest position number on the reagent cooler 5 where the reagent containers 4 are installed is the highest in the order of priority.

As logic for determining the positions on the displacement destination when the reagent containers 4 are displaced from the outer circumferential holder 51 to the positions on the reagent loader 6, the first reagent container 4 is displaced to the position at which no reagent container 4 is installed and which has the lowest position number among all the positions. The positions on the displacement destination are used in an ascending order of the position numbers on the reagent loader 6. While it is described that as for the logic for determining the positions on the reagent loader 6 that is the displacement destination, the order is the ascending order of the position numbers on the reagent loader 6, the order is not limited to the ascending order but may be the descending order of the position numbers on the reagent loader 6 or the like. When the reagent containers 4 are fully installed at all the positions on the reagent loader 6, the next reagent container cannot be unloaded until the reagent container 4 already installed at the position is taken outside from the reagent loader 6.

Mechanism control in the automated analyzer 100 according to the embodiment of the present invention will next be described with reference to FIG. 7. FIG. 7 illustrates timing of operation (motions) per cycle of the outer circumferential holder 51 of the reagent cooler 5, the reagent loader 6, and the reagent container displacement mechanism 20. A horizontal axis indicates time and it is assumed in the present embodiment that one cycle is 12 seconds. Analysis process is established by combining a plurality of cycles each corresponding to one cycle time. The mechanisms to operate vary depending on each cycle time, and the mechanism operation control section 119*d* manages control over those mechanisms, thereby performing the analysis.

During the analysis, the outer circumferential holder 51 is driven to rotate, and sequentially implements following procedures: displacement before stirring of magnetic particles (motion 1) for transporting the reagent container that stores magnetic particles to be close to an access position of the stirring mechanism; displacement after stirring of magnetic particles (motion 2) for displacing the reagent container completed with stirring of the magnetic particles from the access position of the stirring mechanism; and displacement 1 for reagent dispensing (motion 3) and displacement 2 for reagent dispensing (motion 4) for displacing the dispensing target reagent container to an access position of the reagent dispensing mechanism. In addition, the outer circumferential holder 51 implements displacement for reagent loading/unloading (motion 5) for locating the vacant position on the outer circumferential holder 51 to be close to the reagent loader 6 so as to load the reagent container from the reagent loader 6 or for locating the position of the outer circumferential holder 51 that stores the reagent container to be close to the reagent loader 6 so as to unload the reagent container outside of the reagent cooler.

The reagent container displacement mechanism 20 implements displacement before stirring of magnetic particles (motion 6) for drawing the reagent container transported by driving the outer circumferential holder 51 to rotate to the access position of the stirring mechanism, and displacement after stirring of magnetic particles (motion 7) for removing the reagent container completed with stirring of the magnetic particles from the access position of the stirring mechanism. In addition, the reagent container displacement mechanism 20 implements displacement for reagent loading/unloading (motion 8) for displacing the loading target reagent container from the reagent loader to the outer circumferential holder 51 or for displacing the loading target reagent container from the outer circumferential holder 51 to the reagent loader.

Timing (first period 71) for the outer circumferential holder 51 to implement the motions 1 to 4 and for the reagent container displacement mechanism to implement the motions 6 and 7 is secured in one cycle in order to implement the analysis operation. In the first period 71, the reagent loader 6 can vertically move at arbitrary timing in response to an operator's instruction and can implement operation for reagent loading/unloading. Timing (second period 72) for the outer circumferential holder 51 to implement the motion 5 and for the reagent container displacement mechanism to implement the motion 8 is also secured in one cycle in order to implement loading/unloading operation to load and unload the reagent container to or from the reagent reservoir 5. In the second period 72, the reagent loader 6 does not vertically move even if an operator's instruction is present since the reagent container displacement mechanism possibly accesses the reagent loader. While the second period 72 is set between the motions 3 and 4 in the present embodiment, the setting of the second period 72 is not limited thereto and at least one second period may be set in one cycle, i.e., a plurality of second periods 72 may be set in one cycle. Alternatively, the second period 72 may be set once in a plurality of cycles.

As for timing and frequency of setting the second period 72, it is preferable to set at least one second period 72 in one cycle time since the target reagent container 4 is possibly in a used condition (unusable condition as the reagent condition) when, for example, second reagent dispensing is implemented once among analysis steps. In the present embodiment, one second period 72 is set in one cycle time. However, in a case of the automated analyzer in which the number of positions of the reagent loader 6 is five or more, the reagent containers 4 are replaced frequently during the analysis, and many reagent containers 4 can be displaced for loading/unloading in a short time, the number of times of implementing the operation for displacement for reagent loading/unloading may be increased to the number such as two or three, while ensuring that the analysis operation and the use of the mechanisms do not overlap. If one second period 72 is set in one cycle, either loading operation or unloading operation is implemented in the cycle. If a plurality of second periods 72 are set in one cycle, the second periods may be used individually for loading and unloading such as one second period for unloading and the other second period for loading.

If there is no reagent container to be loaded or unloaded, neither the outer circumferential holder nor the reagent container displacement mechanism operates in the second period.

Setting the first period and the second period in one cycle enables the displacement operation for reagent loading/unloading to be implemented at the timing of receiving the operator's instruction via means such as the operation screen or the loader switch.

Figure 8:
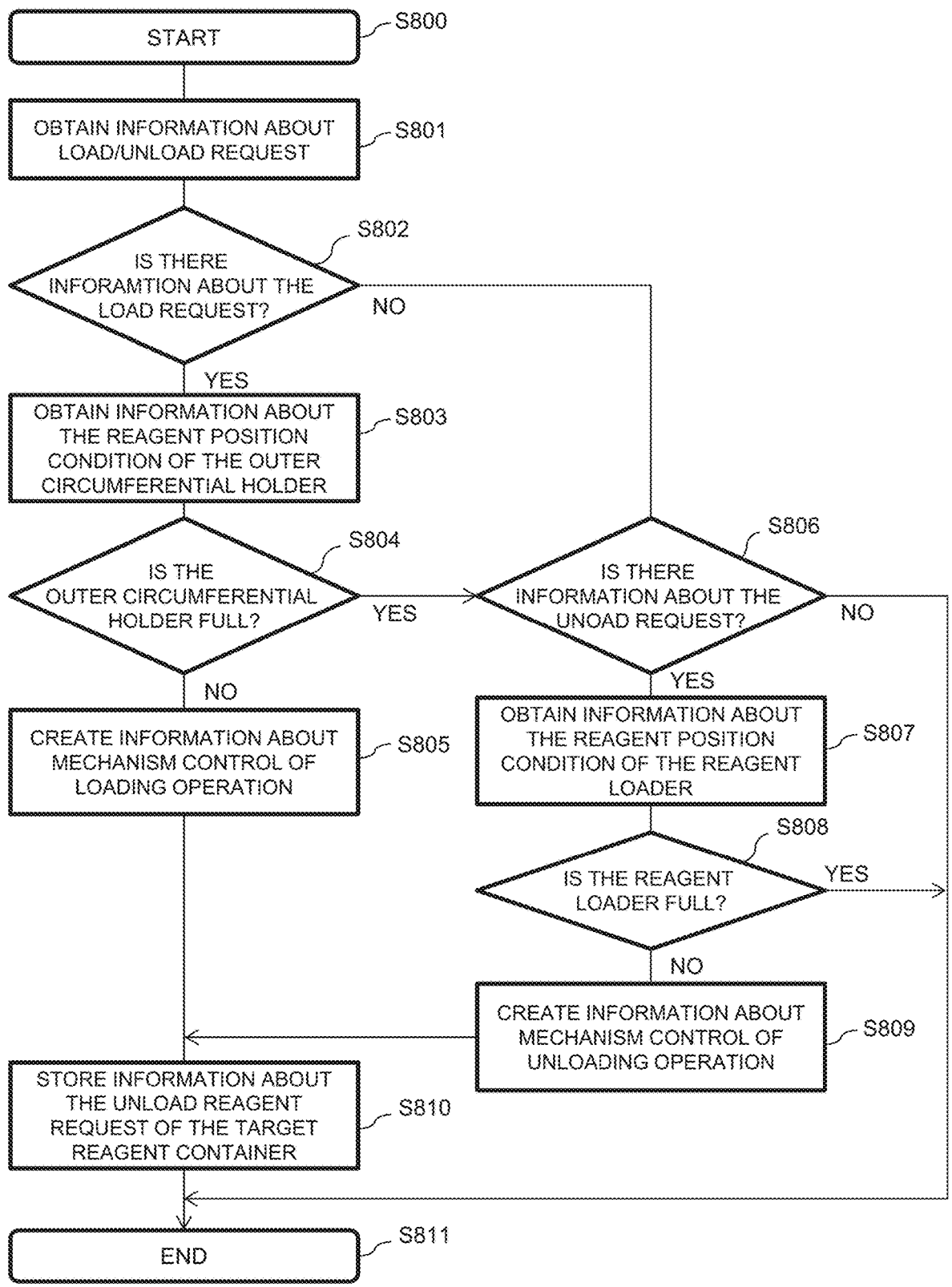
FIG. 8 is a flowchart diagram illustrating logic for determining switchover between operation for loading the reagent container and operation for unloading operation of the reagent container in the automated analyzer according to the embodiment of the present invention.

FIG. 8 illustrates a flow for determining which is implemented, the loading operation of the reagent container 4 or the unloading operation thereof if one second period 72 is set in one cycle.

First, when the timing at which loading/unloading of the reagent container can be implemented starts, the mechanism operation control section 119*d* obtains the information about the load reagent request and the information about the unload reagent request from the reagent loading/unloading information storage section 119*f* (Step S801). The mechanism operation control section 119*d* confirms whether there is a load reagent request from the information about the load reagent request (Step S802).

When there is the load reagent request for the target reagent container 4 (Step S802; YES), the mechanism operation control section 119*d* obtains the information about the reagent position condition on the reagent cooler 5 from the reagent position information storage section 119*h* (Step S803). The mechanism operation control section 119*d* confirms whether all the positions are fully used in the outer circumferential holder 51 from the obtained information about the reagent position condition on the reagent cooler 5 (Step S804).

If all the positions are not fully used in the reagent cooler 5 (Step S804; NO), the mechanism operation control section 119*d* creates information about mechanism control of reagent loading operation on the reagent cooler 5 and the reagent container displacement mechanism 20 (Step S805), and stores the information about the mechanism control in the mechanism control information storage section 119*i* (Step S810).

If there is no information about the load reagent request in Step S802 (Step S802; NO) or if all the positions are fully used in the reagent cooler 5 in Step S804 (Step S804; YES), the mechanism operation control section 119*d* confirms whether there is an unload reagent request from the information about the unload reagent request obtained in Step S801 (Step S806). If there is no unload reagent request for the target reagent container 4 (Step S806; NO), the process is ended.

If there is the unload reagent request for the target reagent container 4 (Step S806; YES), the mechanism operation control section 119*d* obtains the information about the reagent position condition on the reagent loader 6 from the reagent position information storage section 119*h* (Step S807). The mechanism operation control section 119*d* confirms whether all the positions are fully used in the reagent loader 6 from the obtained information about the reagent position condition on the reagent loader 6 (Step S808). If all the positions are fully used in the reagent loader 6 (Step S808; YES), the process is ended.

If all the positions are not fully used in the reagent loader 6 (Step S808; NO), the mechanism operation control section 119*d* creates information about mechanism control of reagent unloading operation on the reagent cooler 5 and the reagent container displacement mechanism 20 (Step S809), and stores the information about the mechanism control in the mechanism control information storage section 119*i* (Step S810).

If the reagent containers 4 are fully installed in all the positions on the outer circumferential holder 51 of the reagent cooler 5 in the automated analyzer 100 as a precondition, a new reagent cannot be loaded to the analyzer 100. To prevent such a condition, the automated analyzer according to the present invention is configured such that whenever there is a reagent container that becomes unusable because, for example, none of the reagents is left or the reagent has expired, or there is a reagent container instructed to be unloaded by a user is automatically displaced from the outer circumferential holder 51 to the reagent loader 6 using the second period described above to secure as many vacant positions as possible on the outer circumferential holder 51.

By doing so, when the user instructs the reagent loader 6 to move upward by depression of the loader switch or the like, then the reagent loader 6 moves upward, and the reagent container 4 stored in the position on the reagent loader 6 is unloaded outside of the reagent cooler 5. After the vacant position is secured on the outer circumferential disk of the reagent cooler 5 by the operation described above, the user installs the reagent container 4 to be loaded to the reagent cooler 5 at the position and instructs the reagent loader 6 to move downward, thereby making it possible to load the reagent container 4 into the reagent cooler 5.

Furthermore, the unloading target reagent container is displaced to the vacant position on the reagent loader 6 whenever the unloading target reagent container occurs. Therefore, even if the reagent container instructed to be loaded and the reagent container instructed to be unloaded are present in the reagent cooler, it is possible to give higher priority to the displacement of the reagent container instructed to be loaded and to promptly supplement the necessary reagent container.

Moreover, before start of the displacement for the reagent loading or unloading to/from the reagent cooler 5, the information about the load reagent request or the information about the unload reagent request from the reagent loading/unloading management section 119a or the input section 19c is stored in the reagent loading/unloading information storage section 119f. Therefore, the mechanism operation control section 119d can control the reagent cooler 5 and the reagent container displacement mechanism 20 to operate to load/unload the reagent container 4 certainly once per cycle time. While it is described in the present embodiment that the automated analyzer 100 is an automated immune analyzer, the automated analyzer 100 may be a biochemical automated analyzer, and contents of the analysis operation performed by the reagent cooler 5, the reagent loader 6, and the reagent container displacement mechanism 20 vary depending on analysis steps and configurations of the mechanisms.

A screen used when the operator confirms whether the reagent container 4 is loadable or unloadable will next be described with reference to FIG. 9. The display section 19b includes the reagent loadable/unloadable display section 119k, and the reagent loadable/unloadable display section 119k includes a reagent loadable/unloadable confirmation screen 22.

Figure 9:
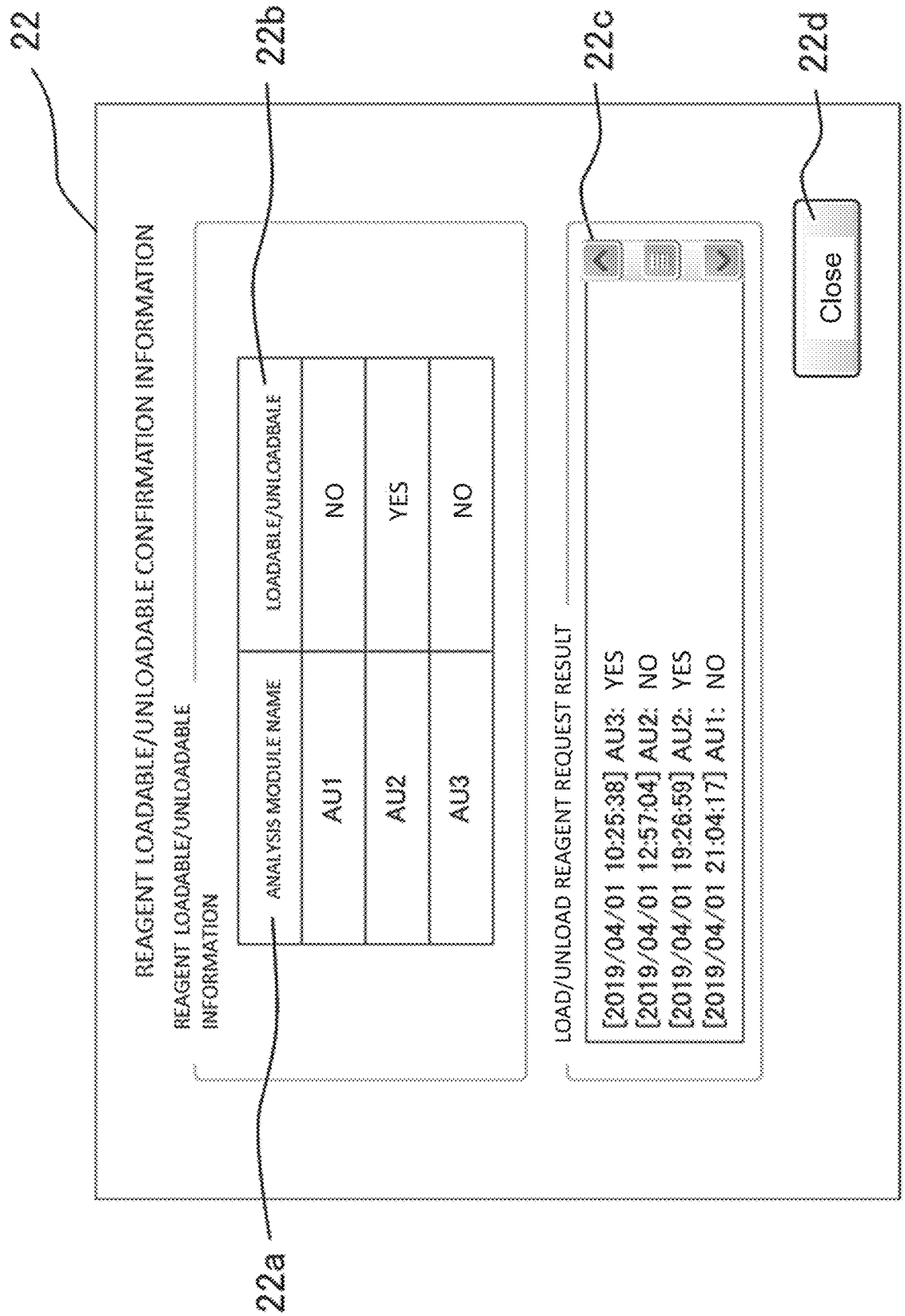
FIG. 9 is an explanatory diagram of a reagent loadable/unloadable confirmation screen used in the automated analyzer according to the embodiment of the present invention.

As shown in FIG. 9, the reagent loadable/unloadable confirmation screen 22 includes an analyzer name display section 22a, a reagent loadable/unloadable information display section 22b, a load/unload reagent request result display section 22c, and a screen close button 22d.

The reagent loadable/unloadable confirmation screen 22 can be opened from the display section 19b and displays reagent loadable/unloadable information and a load/unload reagent request result. The operator can close the reagent loadable/unloadable confirmation screen 22 by depressing the screen close button 22d. The reagent loadable/unloadable information displayed on the reagent loadable/unloadable confirmation screen 22 is configured with the analyzer name display section 22a and the reagent loadable/unloadable information display section 22b. The operator can confirm the reagent loadable/unloadable information per analysis module by referring to the reagent loadable/unloadable confirmation screen 22.

As the load/unload reagent request result on the reagent loadable/unloadable confirmation screen 22, a date, time, each target analysis module, and the load/unload reagent request result are displayed on the load/unload reagent request result display section 22c when the operator issues a load/unload reagent request to the automated analyzer 100 via the reagent loader switch 21. It is possible to confirm previous request process results by scrolling the load/unload reagent request result display section 22c.

The reagent loading/unloading management section 119a obtains information about a control condition on each mechanism from the mechanism operation control section 119d and obtains information about an analyzer condition from the analyzer condition management section 119e at regular intervals. The reagent loading/unloading management section 119a determines whether the reagent container is loadable or unloadable on the basis of the obtained information, and stores a determination result in the reagent loading/unloading information storage section 119f as the reagent loadable/unloadable information. In this case, if the reagent loadable/unloadable information differs between before update and after update, the reagent loading/unloading management section 119a transmits, to the reagent loadable/unloadable display section 119k, a request to update display of the reagent loadable/unloadable information.

Upon receiving the request to update the display of the reagent loadable/unloadable information, the reagent loadable/unloadable display section 119k updates the reagent loadable/unloadable confirmation screen 22 to display latest reagent loadable/unloadable information in the reagent loadable/unloadable information display section 22b corresponding to each of the analysis modules displayed in the analyzer name display section 22a. The operator can recognize whether the automated analyzer 100 is in a condition of being able to load/unload the reagent container 4 by confirming the reagent loadable/unloadable confirmation screen 22.

While the reagent loadable/unloadable confirmation screen 22 displays both the reagent loadable/unloadable information and the load/unload reagent request result in the embodiment of the present invention, the reagent loadable/unloadable confirmation screen 22 does not necessarily display both of the information but may display only one of the reagent loadable/unloadable information and the load/unload reagent request result, and the two pieces of information may be displayed on different screens.

Figure 10:
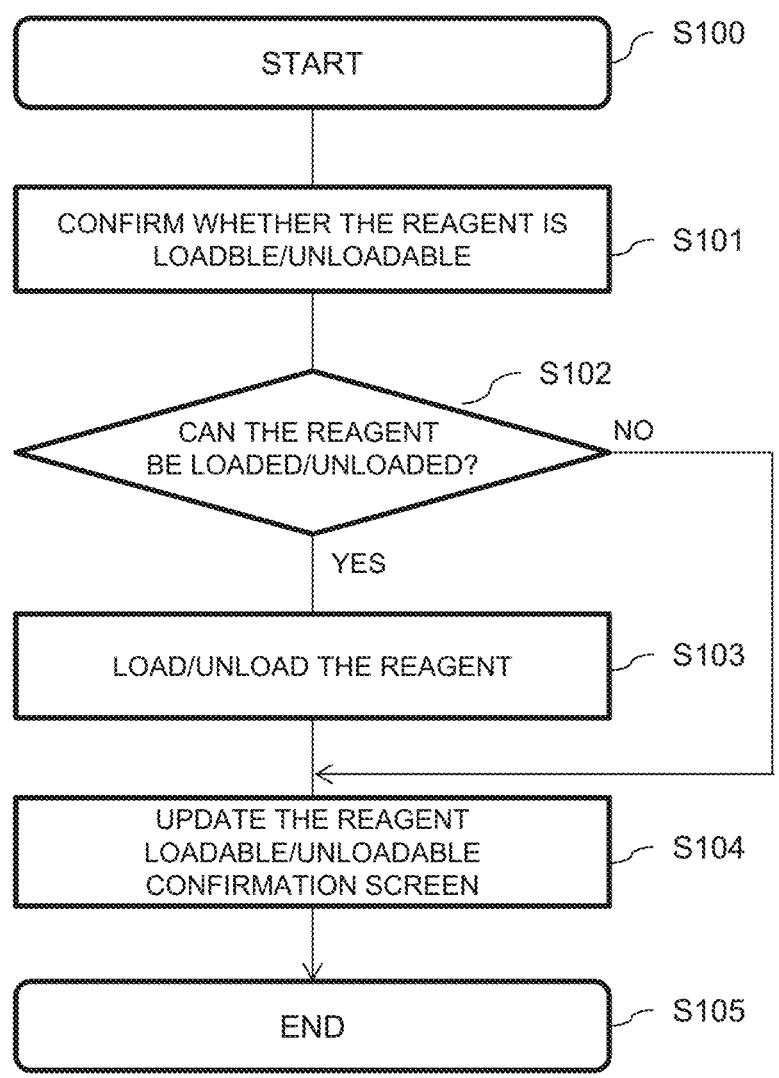
FIG. 10 is a flowchart diagram illustrating process implemented when an operator operates a reagent loader switch in the automated analyzer according to the embodiment of the present invention.

FIG. 10 illustrates a process flow when the operator depresses the reagent loader switch 21 to instruct the automated analyzer 100 to load/unload the reagent container 4.

The operator can instruct the automated analyzer 100 to start loading/unloading the reagent container 4 by operating the reagent loader switch 21. When operator's depressing the reagent loader switch 21 is detected (Step S100), the load/unload reagent request input section 119j requests the reagent loading/unloading management section 119a to start operation for reagent container loading/unloading. The reagent loading/unloading management section 119a obtains the reagent loadable/unloadable information from the reagent loading/unloading information storage section 119f, and confirms whether the reagent container 4 is loadable/unloadable (Step S101). The determination of whether the reagent container 4 is loadable/unloadable is made by referring to the information about the position condition and the information about the analyzer condition. Specifically, the determination depends on whether there is a vacant position on the outer circumferential holder 51 and whether the analyzer condition is a condition in which the operation for the reagent container loading/unloading is possible.

When the reagent container 4 is loadable/unloadable (Step S102; YES), the reagent loading/unloading management section 119a starts process for loading/loading the reagent container 4 (Step S103). The reagent loading/unloading management section 119a then displays, on the reagent loadable/unloadable display section 119k, that is, on the load/unload reagent request result display section 22c on the reagent loadable/unloadable confirmation screen 22, the request result to the effect that the request to load/unload the reagent container 4 has been accepted (Step S104), thus ending the process (Step S105).

On the other hand, when the reagent container 4 is not loadable/unloadable (Step S102; NO), the reagent loading/unloading management section 119a displays, on the reagent loadable/unloadable display section 119k, that is, on the load/unload reagent request result display section 22c on the reagent loadable/unloadable confirmation screen 22, the request result to the effect that the request to load/unload the reagent container 4 is unacceptable (Step S104), and the process for loading/unloading the reagent container 4 is not implemented. The operator can recognize whether the request to load/unload reagent has been accepted by confirming the load/unload reagent request result display section 22c on the reagent loadable/unloadable confirmation screen 22.

While the reagent loader switch 21 is a hardware switch in the embodiment of the present invention, the reagent loader switch 21 is not limited to the hardware switch but may be a software switch such as the key on the screen of the display section 19b.

REFERENCE SIGNS LIST

1: Sample container
2: Sample container rack
3: Rack transport line
4: Reagent container
4a: Inner bottle
4b: Intermediate bottle
4c: Outer bottle
4d: Individual identification label
5: Reagent cooler
51: Outer circumferential holder
52: Inner circumferential holder
53: Position
6: Reagent loader
6a: Reagent loading position
6b: RFID read-out position
6c: Reagent installation position
7: Reagent cooler cover
7a: Reagent cooler cover opening
8: Reaction container
9: Incubator disk
10: Sample dispensing mechanism
11: Reagent dispensing mechanism
12: Reaction container/sample dispensing chip storage section
13: Reaction container/sample dispensing chip storage section
15: Disposal hole
16: Transport mechanism
16a: Chip attachment position
17a, 17b: Nozzle
18a, 18b: Detection unit
19: Control section
19a: Controller
119a: Reagent loading/unloading management section
119b: Reagent condition management section
119c: Reagent position management section
119d: Mechanism operation control section
119e: Analyzer condition management section
19b: Display section
119k: Reagent loadable/unloadable display section
19c: Input section
119j: Load/unload reagent request input section
19d: Storage section
119f: Reagent loading/unloading information storage section
119g: Mounted reagent information storage section
119h: Reagent position information storage section
119i: Mechanism control information storage section
20: Reagent container displacement mechanism
21: Reagent loader switch
22: Reagent loadable/unloadable confirmation screen
22a: Analyzer name display section
22b: Reagent loadable/unloadable information display section
22c: Load/unload reagent request result display section
22d: Screen close button
100: Automated analyzer
71: First period
72: Second period

The invention claimed is:

1. An automated loading/unloading device for an analyzer comprising:

a reagent cooler for housing a reagent holder, including first and second reagent holders, and a reagent loader, the first and second reagent holders cooling and holding a plurality of reagent containers, each of which is configured to contain a reagent that is added to a sample in a reaction container to allow for analysis of the sample by the analyzer, the second reagent holder holding the reagent containers so as to be movable in the reagent cooler, the first reagent holder fixedly holding the reagent containers, and the reagent loader moving with respect to the reagent cooler in order to load and unload the reagent containers to and from the reagent cooler;

a reagent cooler cover which covers an upper surface of the reagent cooler and has an opening through which the reagent loader can pass;

a reagent container displacement mechanism for displacing the reagent containers between the reagent holder and the reagent loader, and between the reagent holder and a stirring position adjacent to a position of the first reagent holder in the reagent cooler;

a magnetic particle stirring mechanism for applying a stirring process to a reagent container at the stirring position;

an input device that allows an operator to input instructions to control displacement of the reagent loader; and a controller programmed to control operation of the second reagent holder, the reagent loader, and the reagent container displacement mechanism in cycles, each cycle including a first period for implementing an operation for the analysis of the sample and a second period for implementing an operation for loading/unloading the reagent containers, based on instructions received from the input device, wherein, in the first period of each cycle, the controller controls:

the second reagent holder to transport the reagent container to the stirring position of the magnetic particle stirring mechanism for the stirring process, to displace the reagent container away from the stirring position of the magnetic particle stirring mechanism after the stirring process, to displace the reagent container to an access position of the reagent dispensing mechanism for dispensing a first reagent in a first reagent dispensing operation, and to displace the reagent container to the access position of the reagent dispensing mechanism for dispensing a second reagent in a second reagent dispensing operation;

the reagent container displacement mechanism to displace the reagent container from the access position of the reagent dispensing mechanism to the stirring position, and to displace the reagent container after stirring from the stirring position to the access position of the stirring reagent dispensing mechanism; and the reagent loader to move upon instruction from the input device to load or unload the reagent container to and from the reagent cooler; and wherein, in the second period of each cycle, the controller controls:

the second reagent holder to move such as to locate a vacant position close to the reagent loader for preparing the loading of the reagent container or to locate the position of the reagent container to be unloaded close to the reagent loader for preparing the unloading of the reagent container; and the reagent container displacement mechanism to displace the reagent container from the reagent loader to the second reagent holder, or to displace the reagent container from the second reagent holder to the reagent loader.

2. The automated loading/unloading device according to claim 1,
wherein the controller receives information about a reagent condition of a reagent container that is being held by the reagent loader.

3. The automated loading/unloading device according to claim 1,
wherein the controller controls loading and unloading of a reagent based on conditions the first reagent container including a loadable condition in which a target reagent container can be loaded into the reagent holder, a temporarily not loadable condition in which the target reagent container cannot be loaded into the reagent holder temporarily, and a continuously not loadable condition in which the target reagent container cannot be loaded into the reagent holder at any time.

4. The automated loading/unloading device according to claim 1,
wherein the controller exercises control so as to displace the first reagent container from the reagent holder to the reagent loader in favor of a second reagent container selected by the operator.

5. The automated loading/unloading device according to claim 1, further comprising:
a storage in which information about whether the first reagent container can or cannot be loaded to/unloaded from a device is stored; and
a display in which an indication of whether the first reagent container can or cannot be loaded to/unloaded from the device is displayed.

* * * * *